United States Patent
Lindacher et al.

(10) Patent No.: US 7,036,931 B2
(45) Date of Patent: May 2, 2006

(54) OPHTHALMIC LENSES

(75) Inventors: Joseph Michael Lindacher, Lawrenceville, GA (US); Courtney Flem Morgan, Alpharetta, GA (US)

(73) Assignee: Novartis AG, Basel (CH)

(*) Notice: Subject to any disclaimer, the term of this patent is extended or adjusted under 35 U.S.C. 154(b) by 30 days.

(21) Appl. No.: 10/762,039

(22) Filed: Jan. 21, 2004

(65) Prior Publication Data

US 2004/0156013 A1    Aug. 12, 2004

Related U.S. Application Data

(60) Provisional application No. 60/443,400, filed on Jan. 29, 2003.

(51) Int. Cl.
  G02C 7/04       (2006.01)
  A61B 18/18      (2006.01)
  A61F 2/16       (2006.01)

(52) U.S. Cl. .............. 351/161; 351/160 R; 351/160 H; 351/177; 606/5; 623/6.11

(58) Field of Classification Search ............ 351/160 H, 351/160 R, 161, 162, 177; 606/5; 623/6.11
See application file for complete search history.

(56) References Cited

U.S. PATENT DOCUMENTS

| | | | |
|---|---|---|---|
| 4,580,882 A | 4/1986 | Nuchman et al. | 351/161 |
| 4,618,227 A | 10/1986 | Bayshore | 351/161 |
| 4,642,112 A | 2/1987 | Freeman | 623/6 |
| 5,050,981 A * | 9/1991 | Roffman | 351/177 |
| 5,691,797 A | 11/1997 | Seidner et al. | 351/161 |
| 5,764,332 A | 6/1998 | Kranhouse | 351/43 |
| 6,082,856 A * | 7/2000 | Dunn et al. | 351/160 H |
| 6,457,826 B1 | 10/2002 | Lett | 351/161 |
| 2002/0105617 A1 | 8/2002 | Norrby et al. | 351/177 |
| 2002/0159025 A1 | 10/2002 | Legerton et al. | 351/160 |
| 2003/0090623 A1 | 5/2003 | Rubinstein et al. | 351/177 |

FOREIGN PATENT DOCUMENTS

| | | |
|---|---|---|
| EP | 1 262 815 | 12/2002 |
| WO | WO 01/92948 | 12/2001 |
| WO | WO 02/08830 | 1/2002 |
| WO | WO 02/083078 | 10/2002 |
| WO | WO 02/088830 | 11/2002 |

OTHER PUBLICATIONS

International Search Report.
International Written Opinion.
European Search Report.

* cited by examiner

Primary Examiner—Scott J. Sugarman
(74) Attorney, Agent, or Firm—Jian S. Zhou (57) ABSTRACT

The present invention provides an ophthalmic lens capable of correcting or minimizing presbyopia, or of functioning used as an anti-myopic lens. The ophthalmic lens can be a contact lens, a phakic intraocular lens or an aphakic intraocular lens. The ophthalmic lens comprises an optical zone, the optical zone having a first surface and an opposite second surface and including a coma-like wavefront aberration oriented vertically from the top to the bottom of the ophthalmic lens. In addition, the present invention provides a method for minimizing/correcting presbyopia or for preventing children's eyes from becoming severely myopic.

56 Claims, 4 Drawing Sheets

OPHTHALMIC LENSES

This application claims the benefit under 35 USC §35 119 (e) of U.S. provisional application No. 60/443,400, filed Jan. 29, 2003, incorporated by reference in its entirety.

The present invention generally relates to ophthalmic lenses including contact lenses and intraocular lenses, which have a vertically oriented coma-like wavefront aberration and are capable of correcting presbyopia or of preventing children's eyes from becoming severely myopic. In addition, the present invention provides a method for minimizing/correcting presbyopia or for preventing children's eyes from becoming severely myopic.

BACKGROUND OF THE INVENTION

It is believed that presbyopia occurs as a person ages when the lens of the eye loses its elasticity, eventually resulting in the eye losing the ability to focus at near distances, such as the normal reading distance, and in some cases at intermediate distances. Presbyopic persons (presbyopes) complain of difficulty performing close tasks. To compensate for presbyopia, ophthalmic lenses are required to be more positively powered or less negatively powered than ophthalmic lenses for the distance correction. Some presbyopic persons have both near vision and far vision defects, requiring segmented bifocal or multifocal lenses or progressive multifocal lenses, instead of single vision lenses, to properly correct their vision.

Large populations of presbyopes also have an astigmatic refractive error. Astigmatism is optical power meridian-dependent refractive error in an eye. This is usually due to one or more refractive surfaces, most commonly the anterior cornea, having a toroidal shape. It may also be due to one or more surfaces being transversely displaced or tilted. Astigmatism is usually regular, which means that the principal (maximum and minimum power) meridians are perpendicular to each other. People with astigmatism have blurred vision at all distances, although this may be worse at distance or near, depending on the type of astigmatism. These people may complain of sore eyes and headaches associated with demanding visual tasks. Astigmatism can be corrected with an astigmatic ophthalmic lens, which usually has one spherical surface and one toroidal (cylindrical) surface.

Myopia and hyperopia, as well as astigmatism, are caused by low order (defocus and astigmatism) and high order aberrations of the eye's optics or incorrect axial length, while presbyopia is caused by loss of elasticity of the crystalline lens on the eye.

Approaches to correct the problem of aberrations in the eye are traditionally exclusive from the approaches for correcting the problem of loss of accommodation in the crystalline lens. The approach to vision correction is to measure and to compensate for only defocus (power) and astigmatism (pupil azimuthal angle dependent power), which cause myopia and astigmatism respectively. Presbyopia is typically treated separately. Aberrations have not been used or considered when correcting the presbyopia. The present invention presents a novel approach for designing and manufacturing lenses for correcting presbyopia through use of aberrations.

SUMMARY OF THE INVENTION

The invention, in one aspect, provides an ophthalmic lens capable of correcting or minimizing presbyopia, or of functioning used as an anti-myopic lens. The ophthalmic lens can be a contact lens, a phakic intraocular lens or an aphakic intraocular lens. The ophthalmic lens comprises an optical zone, the optical zone having a first surface and an opposite second surface and including a coma-like wavefront aberration oriented vertically from the top to the bottom of the ophthalmic lens.

The invention, in another aspect, provides a customized ophthalmic lens comprising an optical zone which, alone or in combination with the optics of an eye, produces a vertically oriented coma-like wavefront aberration.

The invention, in a further aspect, provides a method for correcting/minimizing presbyopia or for preventing a children's eye from becoming severely myopic.

In one embodiment, the method of the invention comprises the step of producing an ophthalmic lens by a manufacturing means, which comprises an optical zone, the optical zone having a first surface and an opposite of second surface and including a coma-like wavefront aberration oriented vertically from the top to the bottom of the ophthalmic lens. The vertically oriented coma-like wavefront aberration is introduced for minimizing/correcting presbyopia or for functioning as an anti-myopic means. The optical zone can also preferably provide optical power for correcting defocus, astigmatism, prism, or combinations thereof.

In another embodiment, the method of the invention comprises the step of reshaping the cornea of an eye to produce a vertically oriented coma-like wavefront aberration.

These and other aspects of the invention will become apparent from the following description of the preferred embodiments taken in conjunction with the following drawings. As would be obvious to one skilled in the art, many variations and modifications of the invention may be effected without departing from the spirit and scope of the novel concepts of the disclosure.

DETAIL DESCRIPTION OF THE INVENTION

A preferred embodiment of the invention is now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Unless defined otherwise, all technical and scientific terms used herein have the same meanings as commonly understood by one of ordinary skilled in the art to which this invention belongs. Generally, the nomenclature used herein and the laboratory procedures are well known and commonly employed in the art. Conventional methods are used for these procedures, such as those provided in the art and various general references.

The optics of the human eye suffer from aberrations that blur vision. Wavefront aberrations of an eye, like an optics or optics system, can be described by different mathematical functions. These mathematical functions can also be used to create models for making optics for correcting these aberrations. Exemplary mathematical functions include conic and quadric functions, polynomials of any degree, Zernike polynomials, exponential functions, trigonometric functions, hyperbolic functions, rational functions, Fourier series, and wavelets. Combinations of these mathematical functions can also be used to describe a front (anterior) surface or a base (posterior) surface of an ophthalmic lens.

Wavefront aberrations generally are quantified in Zernike polynomials which are a set of functions that are orthogonal over the unit circle. They are useful for describing the shape of an aberrated wavefront. There exists several different normalization and numbering schemes for these polynomials. The Zernike polynomials are usually defined in polar coordinates $(\rho,\theta)$, where $\rho$ is the radial coordinate ranging from 0 to 1 and $\theta$ is the azimuthal component ranging from 0 to $2\pi$. Each of the Zernike polynomials consists of three components: a normalization factor, a radial dependent component and an azimuthal dependent component. The radial component is a polynomial, whereas the azimuthal component is sinusoidal. A double indexing scheme is useful for unambiguously describing the functions, with the index n describing the highest power or order of the radial polynomial and the index m describing the azimuthal frequency of the azimuthal component.

Since Zernike polynomials are orthogonal, the aberrations are separable and can be treated as follows. The first order Zernike modes are the linear terms. The second order Zernike modes are the quadratic terms, correspond to power and astigmatism. The third order Zernike modes are the cubic terms, which correspond to the coma and trefoil. The fourth order Zernike modes spherical aberration, secondary astigmatism and quadrafoil. The fifth Zernike modes are the higher-order, irregular aberrations. Local irregularities in the wavefront within the pupil are represented by these higher-order Zernike.

A table of the proposed OSA Standard (Optical Society of America) Zernike Polynomials up to $7^{th}$ order is displayed below (More information on Zernike polynomials is available on http://color.eri.harvard.edu/standardization/standards TOPS4.pdf).

Table of Zernike Polynomials in Polar Coordinates up to $7^{th}$ order (36 terms)

| j | n | m | $Z^m_n(\rho, \theta)$ |
|---|---|---|---|
| 0 | 0 | 0 | 1 |
| 1 | 1 | -1 | $2\rho \sin\theta$ |
| 2 | 1 | 1 | $2\rho \cos\theta$ |
| 3 | 2 | -2 | $\sqrt{6}\,\rho^2 \sin 2\theta$ |
| 4 | 2 | 0 | $\sqrt{3}\,(2\rho^2 - 1)$ |
| 5 | 2 | 2 | $\sqrt{6}\,\rho^2 \cos 2\theta$ |
| 6 | 3 | -3 | $\sqrt{8}\,\rho^3 \sin 3\theta$ |
| 7 | 3 | -1 | $\sqrt{8}\,(3\rho^3 - 2\rho) \sin\theta$ |
| 8 | 3 | 1 | $\sqrt{8}\,(3\rho^3 - 2\rho) \cos\theta$ |
| 9 | 3 | 3 | $\sqrt{8}\,\rho^3 \cos 3\theta$ |
| 10 | 4 | -4 | $\sqrt{10}\,\rho^4 \sin 4\theta$ |
| 11 | 4 | -2 | $\sqrt{10}\,(4\rho^4 - 3\rho^2) \sin 2\theta$ |
| 12 | 4 | 0 | $\sqrt{5}\,(6\rho^4 - 6\rho^2 + 1)$ |
| 13 | 4 | 2 | $\sqrt{10}\,(4\rho^4 - 3\rho^2) \cos 2\theta$ |
| 14 | 4 | 4 | $\sqrt{10}\,\rho^4 \cos 4\theta$ |
| 15 | 5 | -5 | $\sqrt{12}\,\rho^5 \sin 5\theta$ |
| 16 | 5 | -3 | $\sqrt{12}\,(5\rho^5 - 4\rho^3) \sin 3\theta$ |
| 17 | 5 | -1 | $\sqrt{12}\,(10\rho^5 - 12\rho^3 + 3\rho) \sin\theta$ |
| 18 | 5 | 1 | $\sqrt{12}\,(10\rho^5 - 12\rho^3 + 3\rho) \cos\theta$ |
| 19 | 5 | 3 | $\sqrt{12}\,(5\rho^5 - 4\rho^3) \cos 3\theta$ |
| 20 | 5 | 5 | $\sqrt{12}\,\rho^5 \cos 5\theta$ |
| 21 | 6 | -6 | $\sqrt{14}\,\rho^6 \sin 6\theta$ |
| 22 | 6 | -4 | $\sqrt{14}\,(6\rho^6 - 5\rho^4) \sin 4\theta$ |
| 23 | 6 | -2 | $\sqrt{14}\,(15\rho^6 - 20\rho^4 + 6\rho^2) \sin 2\theta$ |
| 24 | 6 | 0 | $\sqrt{7}\,(20\rho^6 - 30\rho^4 + 12\rho^2 - 1)$ |
| 25 | 6 | 2 | $\sqrt{14}\,(15\rho^6 - 20\rho^4 + 6\rho^2) \cos 2\theta$ |
| 26 | 6 | 4 | $\sqrt{14}\,(6\rho^6 - 5\rho^4) \cos 4\theta$ |
| 27 | 6 | 6 | $\sqrt{14}\,\rho^6 \cos 6\theta$ |
| 28 | 7 | -7 | $4\,\rho^7 \sin 7\theta$ |
| 29 | 7 | -5 | $4\,(7\rho^7 - 6\rho^5) \sin 5\theta$ |
| 30 | 7 | -3 | $4\,(21\rho^7 - 30\rho^5 + 10\rho^3) \sin 3\theta$ |
| 31 | 7 | -1 | $4\,(35\rho^7 - 60\rho^5 + 30\rho^3 - 4\rho) \sin\theta$ |
| 32 | 7 | 1 | $4\,(35\rho^7 - 60\rho^5 + 30\rho^3 - 4\rho) \cos\theta$ |
| 33 | 7 | 3 | $4\,(21\rho^7 - 30\rho^5 + 10\rho^3) \cos 3\theta$ |
| 34 | 7 | 5 | $4\,(7\rho^7 - 6\rho^5) \cos 5\theta$ |
| 35 | 7 | 7 | $4\,\rho^7 \cos 7\theta$ |

Defocus (myopia and hyperopia), astigmatism and prism can be classified as low-order aberrations. "High-order" aberrations of an eye as used herein refers to chromatic wavefront aberrations beyond defocus and astigmatism, namely, third order, fourth order, fifth order, and higher order wavefront aberrations. Unlike defocus (myopia and hyperopia), astigmatism and prism, presbyopia is not caused by aberrations. Presbyopia is caused by loss of accommodation of the crystalline lens on the eye, i.e., the crystalline lens loses its elasticity and, therefore, it cannot change shape as readily to bring light to a focus on the retina. It has been found that this loss of depth of focus can be minimized by adding a vertically oriented coma-like wavefront aberration to the eye's optics.

It is believed that a contact lens with a vertically oriented coma-like wavefront aberration may be served as an anti-myopic lens for children. Currently, children become increasingly more myopic according to some recent studies. This is partly due to the fact that children engages extensively on a daily basis close reading activities, for example, such as playing video games or the like, and therefore their eyes are in an accommodation state for extended periods of time. These condition of keeping the eyes almost constantly under stress in thought to interfere with the emmetropization process. By having a vertically oriented coma-like wavefront aberration, a contact lens may provide added power in the lower portion of the optical zone for near vision, decrease the accommodation level of an eye required for close reading activities, and thereby prevent the eye from becoming severely myopic.

A "coma-like wavefront aberration" refers to a wavefront aberration which is, or is an equivalent of, a wavefront aberration described by any one of third order, fifth order, seventh order Zernike coma-like terms, and combinations thereof in the proposed OSA Standard (Optical Society of America) Zernike Polynomials.

In one aspect, the invention provides an ophthalmic lens, such as a contact lens, a phakic intraocular lens, or an aphakic intraocular lens, which is capable of correcting or minimizing presbyopia, or can be used as anti-myopic lens. An ophthalmic lens of the invention comprises an optical zone, the optical zone having a first surface and an opposite second surface and a coma-like wavefront aberration oriented vertically from the top to the bottom of the lens.

Contact lenses of the invention can be either hard or soft lenses. Soft contact lenses of the invention are preferably made from a soft contact lens material, such as a silicon or fluorine-containing hydro-gel or HEMA. It will be understood that any lens material can be used in the production of an ophthalmic lens of the invention.

The optical zone of an ophthalmic lens of the invention is designed according to a mathematical model, or alternative representation, that not only can provide optical power for correcting defocus, astigmatism, prism, or combinations thereof, but also can create an ideal aberration pattern in the optical zone of the lens to correct or minimize the presbyopia or to prevent an eye from becoming more myopic. The ideal aberration pattern is a vertically oriented coma-like aberration. The optical zone created according to the invention has at least one asymmetrical optical surface and an optical power profile varying from the top to the bottom of the optical zone. The lower section of the optical zone has more optical power than the upper section of the optical zone. Typically the sag difference (or the height difference between the apex and any point on the surface) of the asymmetrical surface, across the optical zone, can be on the order of 10 µm or less, but the optical power profile of the optical zone can vary on the order of several diopters.

It is well known to those skilled in the art that, like the optical power, a vertically oriented coma-like wavefront aberration can be introduced in an ophthalmic lens by designing and optimizing the first surface and opposite second surface of the optical zone of the ophthalmic lens. For example, one can first design the first surface of an optical model lens in a form of mathematical description and then design and optimize the second surface of the model lens to impart to the model lens a desired amount of a vertically oriented coma-like wavefront aberrations and an optical power for correcting one or more low-order wavefront aberrations, for example, by using ray tracing techniques. It is understood that either or both of the first and opposite second surface of an optical model lens can be optimized to produce a desired amount of a vertically oriented coma-like wavefront aberration.

The ray tracing technique is well known in the art. Several commercially-available optical design software packages contain ray tracing programs. Exemplary optical design software packages include Zemax from Focus Software, Inc. and Advanced System Analysis program (ASAP) from Breault Research Organization.

An "optical model lens" refers to an ophthalmic lens that is designed in a computer system and generally does not contain other non-optical systems which are parts of an ophthalmic lens. Exemplary non-optical systems of a contact lens include, but are not limited to bevel, lenticular, orientation or stabilization features, and edge that joins the anterior and posterior surfaces of a contact lens. Exemplary non-optical systems of an intraocular lens (phakic or aphakic) include without limitation haptics.

A "bevel" refers to a non-optical surface zone located at the edge of the posterior surface of a contact lens. Generally, the bevel is a significantly flatter curve and is usually blended with the base curve (optical posterior surface) of a contact lens and appears as an upward taper near the edge. This keeps the steeper base curve radius from gripping the eye and allows the edge to lift slightly. This edge lift is important for the proper flow of tears across the cornea and makes the lens fit more comfortable. "A lenticular" refers to a non-optical surface zone of the anterior surface of a contact lens between the optical zone and the edge. The primary function of the lenticular is to control the thickness of the lens edge.

Any mathematical function can be used to describe the first surface and the opposite second surface of the optical zone of an ophthalmic lens, as long as they have sufficient dynamic range which allow the design of that lens to be optimized. Exemplary mathematical functions include conic, biconic and quadric functions, polynomials of any degree, Zernike polynomials, exponential functions, trigonometric functions, hyperbolic functions, rational functions, Fourier series, and wavelets. Preferably, a spline-based mathematical function or a combination of two or more mathematical functions are used to describe the first surface and second surface of an optical zone. The combination of two or more mathematical functions includes preferably Zernike polynomials, more preferably at least one of third, fifth and seventh order coma-like terms.

In one embodiment, at least one of the first and second surface of the optical zone of an ophthalmic lens of the invention can be described by a combination of a biconic function with at least one vertically oriented coma-like Zernike term or equivalents thereof. The magnitude of the vertically oriented Zernike coma coefficient, based on the proposed OSA Zernike standard, is preferably between 0.1 µm RMS (root-mean-square) and 2 µm RMS at a 6 mm diameter optical zone. The optimal value will depend on the degree of presbyopic correction and/or magnitude and orientation of the eye's coma.

In accordance with the invention, at least a vertically oriented third order coma-like Zernike term Z7 (based on the proposed OSA Standard Zernike Polynomials) is preferably used in combination with a biconic function to describe at least one of the first and second surface of the optical zone of an ophthalmic lens of the invention. Such mathematical description can be expressed by the following equation.

$$Z(\rho, \theta) := \frac{(c_x \bullet r^2 + c_y \bullet r^2)}{\left[1 + \sqrt{1 - (1 + k_x) \bullet (c_x^2 \bullet r^2) - (1 + k_y) \bullet c_y^2 \bullet r^2}\right]} + \quad (1)$$
$$Z7 \bullet \sqrt{8} \bullet (3 \bullet \rho^2 - 2) \bullet \rho \bullet \sin(\theta)$$

wherein
$Z(\rho,\theta)$ describes the optical surface,
$c_x$ is the curvature (reciprocal of the radius) in x' direction,
$c_y$ is the curvature (reciprocal of the radius) in y' direction,
$k_x$ x is a conic constant in x' direction,
$k_y$ is a conic constant in y' direction,
r equals to the semi diameter of the optical surface,
$\rho$ is equivalent to the normalized pupil coordinate (r/rmax),
$\theta$ is angular component,
Z7 is coefficient of vertical coma term in RMS (root-mean-square) µm.

Equation (1) is in the form of $Z(\rho, \theta)=A(\rho)+B(\rho, \theta)$, where the first component $A(\rho)$ corrects power and astigmatism and the second component $B(\rho, \theta)$ introduces a coma-like aberration for correcting or minimizing presbyopia. The major and minor axes of the biconic function, x' and y', in general, do not correspond to vertical and horizontal orientations.

Figure 2:
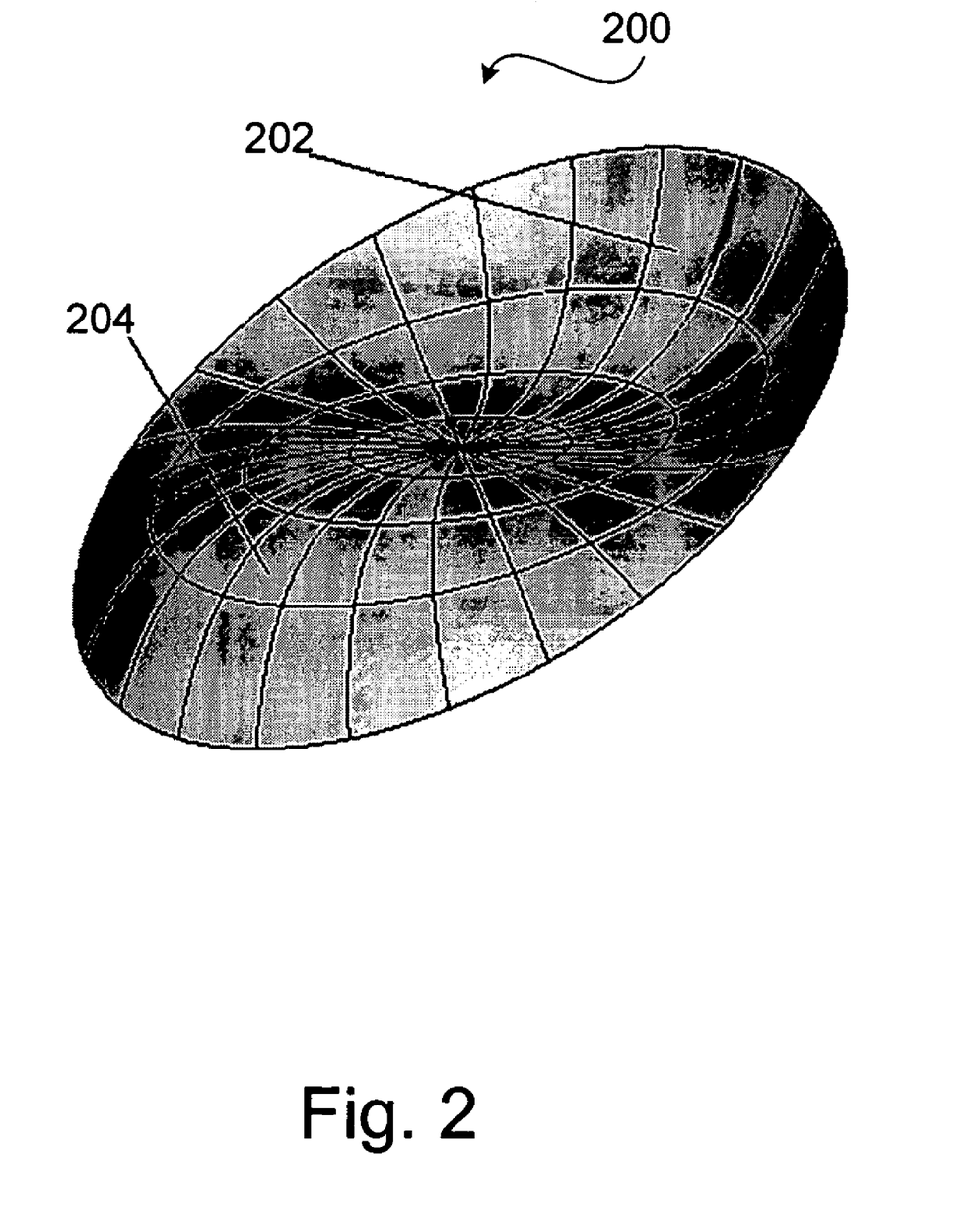
FIG. 2 is an illustration of an optical surface according to a preferred embodiment of the invention.
Figure 3:
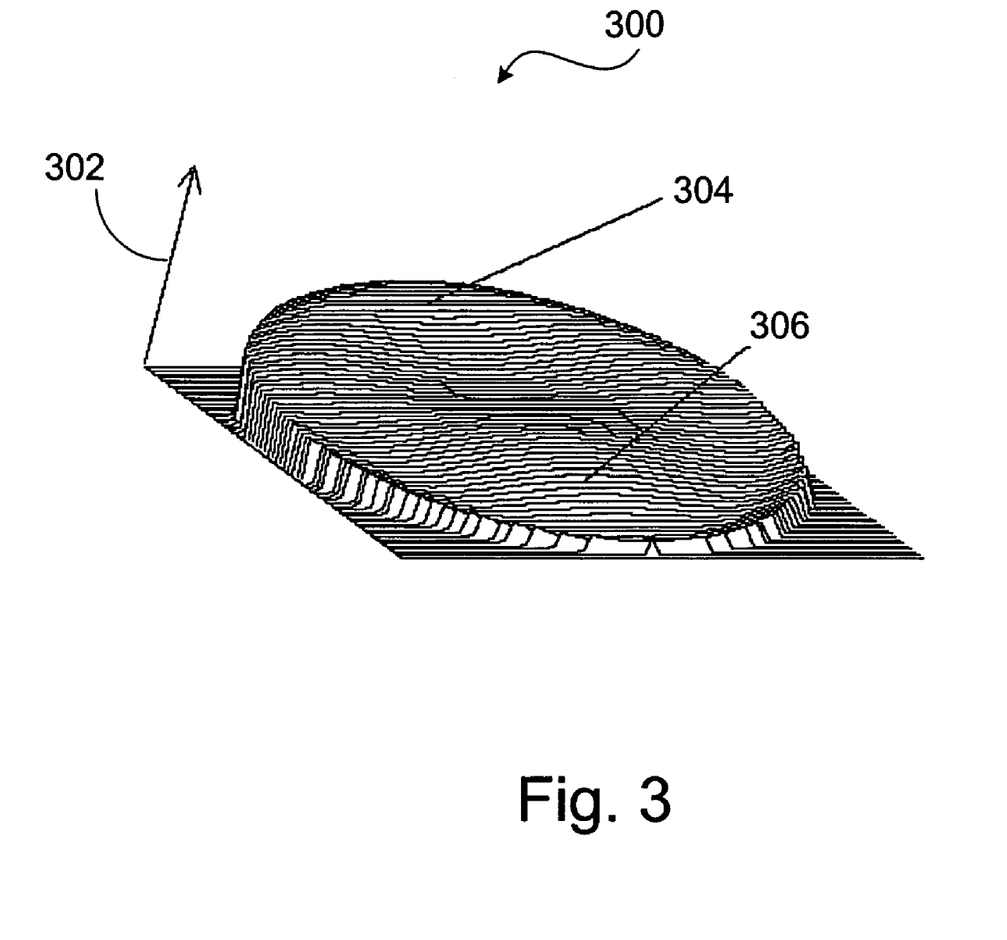
FIG. 3 is an illustration of an optical power profile of an optical surface according to FIG. 2.

Preferably, the value of Z7 in equation (1) is between 0.1 and 2 µm RMS at a 6 mm diameter optical zone to introduce an optimal amount of aberration. The polarity of the value is such that the lower section of the optical zone has more optical power than the upper section of the optical zone as shown in FIGS. 2 and 3.

Alternatively, at least a vertically oriented fifth order coma-like Zernike term Z17 or seventh order coma-like term Z31 (based on the proposed OSA Standard Zernike Polynomials) can also preferably be used in combination with a biconic function to describe at least one of the first and second surface of the optical zone of an ophthalmic lens of the invention.

In another embodiment, at least one of the first and second surface of the optical zone of an ophthalmic lens of the invention can be described by a combination of a conic function with at least one vertically oriented coma-like Zernike term (e.g., Z7, Z17, Z31, or combinations thereof, based on the proposed OSA Standard Zernike Polynomials).

In another embodiment, at least one of the first and second surface of the optical zone of an ophthalmic lens of the invention is an asymmetrical surface with a vertically offset spline-based surface (defined by one or more spline-based functions).

Where an ophthalmic lens of the invention is a contact lens, the contact lens preferably comprises one or more orientation/stabilization features. Any suitable orientation/stabilization features can be used in the invention. Exemplary orientation/stabilization features include, without limitation, a prism ballast or the like that uses a varying thickness profile to control the lens orientation; a faceted surface in which parts of the lens geometry is removed to control the lens orientation; a ridge feature which orients the lens by interacting with the eyelid, double slab-off features which have a top slab-off zone and a bottom slab-off zone zones to maintain the lens orientation on the eye as well as a visual cue on the lenses so that a wearer can insert the lenses in the proper orientation; non-prism ballast features in the peripheral zone of the lens, disclosed in a co-pending U.S. patent application No.60/401,736 filed on Aug. 6, 2002, entitled "Contact lenses" (herein incorporated by reference in its entirety); and the like.

Preferably, the orientation/stabilization features of a contact lens of invention comprises on the anterior surface of the lens a ramped ridge zone, which is described in a copending U.S. patent application No. 60/398/485 filed on Jul. 24, 2002, entitled "Translating Contact Lens Having A Ramped Ridge", herein incorporated by reference in its entirety. The ramped ridge zone is disposed below the optical zone and includes an upper edge, a lower ramped edge, a latitudinal ridge that extends outwardly from the anterior surface, and a ramp that extends dowardly from the lower ramped edge and has a curvature or slope that provides a varying degree of interaction between the ramped ridge zone and the lower eyelid depending on where the lower eyelid strikes the ramped ridge zone. The lower eyelid of the eye is engaged with at least some portion of the ramped ridge zone at all times. Such ramped ridge zone can provide wearer's comfort and also is capable of controlling contact lens position on an eye in primary gaze and/or translating amount across the eye when the eye changes from gazing at an object at a distance to gazing at an object at an intermediate distance or at a nearby object. Preferably, when transforming the design of an optimized optical model lens into a mechanical lens design, some common features of a family of contact lenses can be incorporated.

More preferably, the orientation/stabilization features of a contact lens of invention comprises non-prism ballast features in the peripheral zone of the lens, disclosed in a co-pending U.S. patent application No.60/401,736 (incorporated herein by reference in its entirety. It was discovered that, when a contact lens has in the peripheral zone (non-optical zone surrounding the optical zone) a lens thickness profile characterized by having a thickness which increases progressively from the top of the lens downwardly along each of the vertical meridian and lines parallel to the vertical meridian until reaching a maximum value at a position between the optical zone and the edge zone and then decreases to the edge of the edge zone, such contact lens can be maintained at a predetermined orientation on an eye. Like a conventional lens ballast, such orientation feature works by weighing the lens at the bottom, causing it to come to an equilibrium position on the eye. With such orientation feature, the optical zone of the anterior surface can be designed independently that can provide an optimal visual performance.

A "vertical meridian" refers to an imaginary line running vertically from the top, through the center, to the bottom of a contact lens when said contact lens is maintained at a predetermined orientation on an eye. A "horizontal meridian" refers to an imaginary line running horizontally from the left side, through the center, to the right side of the anterior surface of a contact lens when said contact lens is maintained at a predetermined orientation on an eye. The horizontal and vertical meridians are perpendicular to each other.

Where an ophthalmic lens of the invention is an intraocular lens (phakic or aphakic), the intraocular comprises haptics. Any known suitable haptics can be used in the present invention.

Figure 1A:
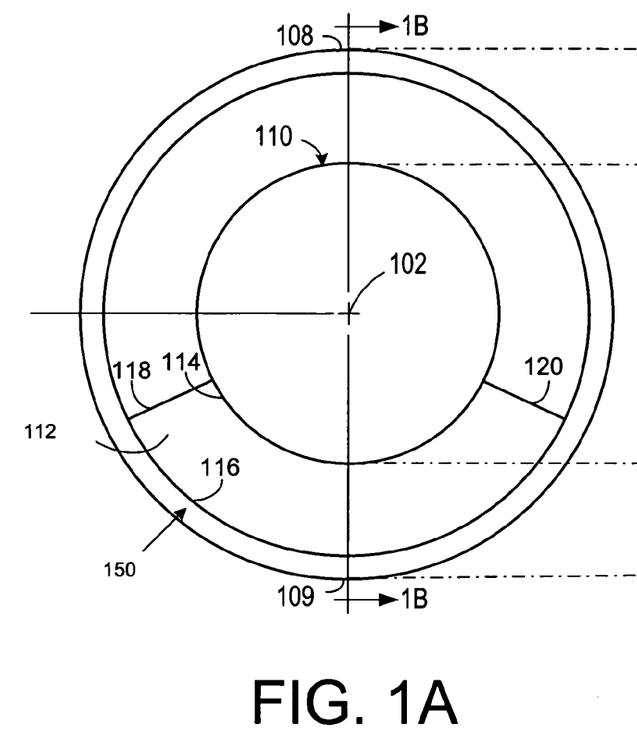
FIG. 1A is an illustration of a contact lens according to a preferred embodiment of the invention.
Figure 1B:
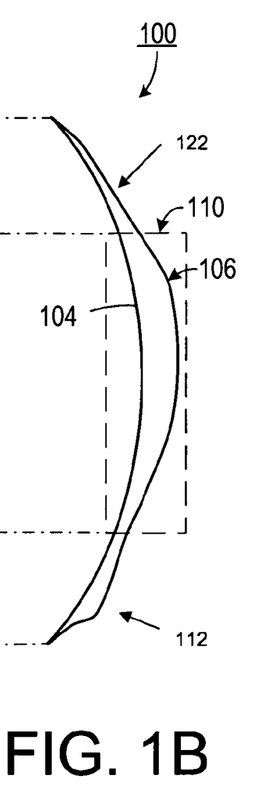
FIG. 1B is a profile of the lens illustrated in FIG. 1A.

FIGS. 1A and 1B illustrate schematically a contact lens 100 according to a preferred embodiment of the invention. Contact lens 100 comprises an anterior surface 106, a posterior surface 104, a top 108, and a bottom 109. The anterior surface 106 has an optical zone 110, a ramp ridge zone 112, a ridge-off zone 122, and a lenticular zone 150.

The optical zone 110 refracts light passing through it. The rays of light, upon passing through the optical zone 110, focus on a real (for hyperopic lenses) or virtual (for myopic lenses) focus point, thus providing a clear vision to a person.

The ramp ridge zone 112 that provides vertical translation support for the lens. The ramp ridge zone 112 has an upper edge 114, a lower edge 116, a first side edge 118 and a second side edge 120. The ramp ridge zone 112 is disposed below the optical zone 110.

The ridge-off zone 122 extends outwardly from the optical zone 110, the first side edge 118 of the ramp ridge zone 110 and the second side edge 120 of the ramp ridge zone 110. The ridge-off zone 112 can add lens rotational stability and improves the comfort of the lens 100. For added comfort and better corneal coverage, the lens 100 may also include a lenticular zone 150, extending radially outward from the ridge-off zone 160 and the lower ramped edge 116 of the ramped ridge zone 112, that tapers to a narrow end.

Figure 4:
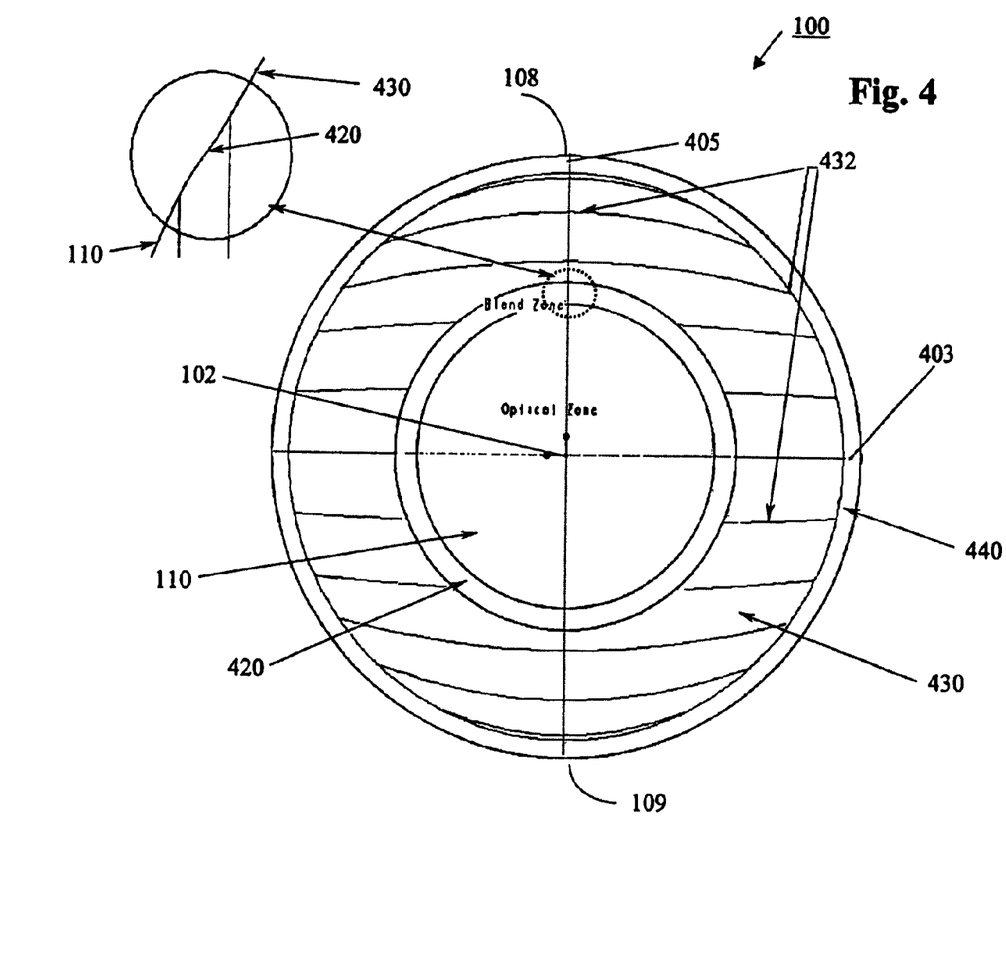
FIG. 4 is an illustration of the anterior surface of a contact lens according to a preferred embodiment of the invention.

FIG. 4 is a front elevational view (the anterior surface) of a contact lens according to another preferred embodiment of the invention. The anterior surface 106 of the contact lens 100 has a center 102, a horizontal meridian 403, a vertical meridian 405, an optical zone 110, a blending zone 420, a peripheral zone 430, and a circular edge zone 440.

The blending zone 420 extends outwardly from the optical zone 110 to the peripheral zone 430. The blending zone 420 has a surface ensuring that the central optical zone 110, the blending zone 420 and the peripheral zone 430 are tangent to each other. The surface of the blending zone 420 is continuous in first and/or second derivative from the outer peripheral edge of the optical zone 110 to the inner peripheral edge of the peripheral zone 430. The surface of the blending zone 420 is described preferably by one or more spline-based mathematical functions.

The peripheral zone 430 has a surface that, in combination with the posterior surface 104, provides in the peripheral zone of the lens a thickness profile which is characterized (1) by having a lens thickness which increases progressively from the top of the lens downwardly along each of the vertical meridian and lines parallel to the vertical meridian until reaching a maximum value at a position between the anterior optical zone and the edge zone and then decreases to the edge of the edge zone, or (2) by having a mirror symmetry with respect to a plane cutting through the vertical meridian, by having a substantially constant thickness in a region around the horizontal meridian and by having a thickness which decreases progressively from the horizontal meridian to the top or bottom of the contact lens along each of the vertical meridian and lines parallel to the vertical meridian.

The peripheral zone 430 preferably includes a series of isolines along which the thickness of the contact lens are substantially constant. One of the isolines coincides with the horizontal meridian 403 running horizontally through the center 102 and the rest isolines preferably are arcs. Each of arcs, which are above the central horizontal isoline, is different from each other and mimics one arc of the peripheral edge of the upper eyelid of the human eye at a given eye-opening position. Each of arcs, which are below the central horizontal isoline, is different from each other and mimics one arc of the peripheral edge of the lower eyelid of the human eye at a given eye-opening position.

It is well known to a person skilled in the art that the upper and lower eyelids of an eye can have a different shaped arc (radius of curvature), depending upon the fully or partially opening or fully closing position of the eye. When an eye is fully closed, both the arcs representing the edge of the upper eyelid and the edge of the lower eyelid are close to a straight line. When an eye is fully opened, both the arcs representing the edge of the upper eyelid and the edge of the lower eyelid have steep curvatures. Such relationship between the curvature of both the arcs representing the edge of the upper eyelid and the edge of the lower eyelid is preferably incorporated in the design of a contact lens of the invention as shown in FIG. 4, namely, closer to the horizontal meridian an isoline, flatter the curvature of the isoline.

The peripheral zone 430 of the anterior surface 106 preferably includes a ramped ridge zone. Preferably, the thickness of the peripheral zone will decrease progressively from the top of the anterior surface downwardly along the vertical meridian 405 and each of lines parallel to the vertical meridian 405 until reaching a maximum value at a position between the optical zone and the edge zone and then decreases to the edge of the edge zone. The thickness of the lens outside of the central optical zone 110 preferably has a mirror symmetry with respect to a plane cutting through the vertical meridian 405.

The circular edge zone 440 extends outwardly from the outer peripheral edge of the peripheral zone 430. The edge zone 440 is tangent to the peripheral zone and, in combination with the posterior surface, provides a substantially uniform thickness which may provide comfortable lens fit on an eye.

FIG. 2 illustrates an optical zone 200 having an optical surface described by equation (1). That surface has a coma-like geometry. The optical zone 200 has an upper section 202 and a lower section 204. The upper section 202 provides distance power for correcting distance vision, such as myopia and hyperopia. The lower section 204 provides add or near power for correcting near vision for individuals with presbyopia.

The power of an optical zone is proportional to the second derivative of a surface. Therefore, an optical zone with a coma-like surface shown in FIG. 2 can have an optical power profile similar to a tilted surface, as shown in FIG. 3.

FIG. 3 illustrates an optical power profile 300 for the optical zone 200. The optical power profile is represented relative to an optical power axis 302. The lower section 204 of the optical zone has more optical power and it is represented by region 304. The upper section 202 has less optical power and it is represented by region 306.

In another aspect, the present invention provides a customized ophthalmic lens which comprises an optical zone which, alone or in combination with the optics of an eye, produce a vertically oriented coma-like wavefront aberration.

A "customized ophthalmic lens", as used herein, means: (1) an ophthalmic lens that is designed using input of aberration measurements of an eye of an individual; and/or (2) an ophthalmic lens that has one of the surfaces accommodating the corneal topography of an eye of an individual.

The wavefront aberrations of an eye of an individual can be determined by any suitable methods known to one skilled in the art, including without limitation, Shack-Hartmann techniques, Tscherning techniques, retinal raytracing techniques, and spatially-resolved refractometer techniques. For example, Liang et al. in J. Optical Soc. Am. 11: 1–9, the entirety of which are herein incorporated by reference, teach how to determine wavefront aberrations of an eye at various pupil diameters using a Hartmann-Shack system.

Preferably, corneal topographic data of an eye of an individual can be used to design the posterior surface of a customized contact lens, to accommodate the corneal topography of that eye or a corneal topography statistically represent a segment of population. Corneal topographic data can be acquired using a corneal topographer or videokeratoscope. Corneal topography data may be in any forms suitable for use in designing an ophthalmic lens. Exemplary forms include, but are not limited to, Zernike polynomials, point cloud data and the like. Preferably, corneal topography data is in a form in which the wavefront aberrations of an eye are quantified. The corneal topography data can also be an averaged corneal topography derived from population studies. Such averaged corneal topography data may represent a segment of population and can be used to design the posterior surface of a customized contact lens.

A contact lens, which has a posterior surface capable of accommodating the corneal topography of an eye or a corneal topography statistically represent a segment of population, will provide a good or adequate fit to the cornea of that eye and therefore enhance the wearer's comfort. It is believed that the posterior surface of a contact lens does not need to match perfectly the corneal topography of an eye. A perfect match means the posterior surface of a contact lens is exactly superimposable on a corneal topography. A contact lens, which has a posterior surface perfectly matching the corneal topography of an eye, may have inadequate on-eye movement of the lens and may have an adverse impact on wearer's comfort.

Based on aberration measurements of an eye of an individual, the optical zone of an customized ophthalmic lens is designed in various ways not only to correct low order aberrations (defocus, astigmatism, and prism) but also to create, alone or in combination with the optics of an eye, a vertically oriented coma-like wavefront aberration.

Where an eye of an individual may have high order wavefront aberrations including a vertically-orientated coma-like wavefront aberration, an ophthalmic lens of the invention can be designed to correct or minimize wavefront aberration other than the vertically oriented coma-like aberration. Optionally, a vertically oriented coma-like wavefront aberration is introduced in the ophthalmic lens to increase the overall amount of vertically oriented coma-like wavefront aberration of the ophthalmic lens plus the eye.

Where an eye of an individual typically does not have any dominant vertically oriented coma-like wavefront aberration but has other higher order wavefront aberrations, an ophthalmic lens of the invention can be designed to correct all or parts of each of dominant high order wavefront aberrations so as to obtain a vertically oriented coma-like wavefront aberration.

A customized ophthalmic lens of the invention can be designed and produced preferably by using methods described in a published PCT patent application No. WO 02/088830, herein incorporated by reference in its entirety.

An ophthalmic lens or a customized ophthalmic lens of the invention can be designed using any known, suitable optical design system. Exemplary optical computer aided design systems for designing an optical model lens includes, but are not limited to ZEMAX (Focus Software, Inc.). Preferably, the optical design will be performed using ZEMAX (Focus Software, Inc.). The design of the optical model lens can be transformed by, for example, a mechanical computer aided design (CAD) system, into a set of mechanical parameters for making a physical lens. Any know, suitable mechanical CAD system can be used in the invention. The design of an optical model lens may be translated back and forth between the optical CAD and mechanical CAD systems using a translation format which allows a receiving system, either optical CAD or mechanical CAD, to construct NURBs (nonuniform rational B-splines) or Beizier surfaces of an intended design. Exemplary translation formats include, but are not limited to, VDA (verband der automobilindustrie) and IGES (Initial Graphics Exchange raphics Exchange Specification). By using such translation formats, overall surface of lenses can be in a continuous form that facilitates the production of lenses having radially asymmetrical shapes. Beizier and NURBs surface are particular advantageous for a lens having a plurality of zones including optical zone and non-optical zones because multiple zones can be blended, analyzed and optimized. More preferably, the mechanical CAD system is capable of representing precisely and mathematically high order surfaces. An example of such mechanical CAD system is Pro/Engineer from Parametric Technology.

When transforming the design of an optical model lens into a set of mechanical parameters, common feature parameters of a family of ophthalmic lenses can be incorporated in the lens designing process. Examples of such parameters include shrinkage, non-optical edge zone and its curvature, center thickness, range of optical power, and the like.

An ophthalmic lens of the invention may be produced by any convenient manufacturing means, including, for example, a computer-controllable manufacturing device, molding or the like. A "computer controllable manufacturing device" refers to a device that can be controlled by a computer system and that is capable of producing directly an ophthalmic lens or an optical tools for producing an ophthalmic lens. Any known, suitable computer controllable manufacturing device can be used in the invention. Exemplary computer controllable manufacturing devices includes, but are not limited to, lathes, grinding and milling machines, molding equipment, and lasers. Preferably, a computer controllable manufacturing device is a two-axis lathe with a 45° piezo cutter or a lathe apparatus disclosed by Durazo and Morgan in U.S. Pat. No. 6,122,999 (herein incorporated by reference in its entirety), or is a numerically controlled lathe, for example, such as Optoform® ultra-precision lathes (models 30, 40, 50 and 80) having Variform® or Varimax piezo-ceramic fast tool servo attachment from Precitech, Inc.

Preferably, contact lenses are molded from contact lens molds including molding surfaces that replicate the contact lens surfaces when a lens is cast in the molds. For example, an optical cutting tool with a numerically controlled lathe may be used to form a metallic optical tool incorporating the features of the anterior surface of a contact lens of the invention. The tool is then used to make anterior surface molds that are then used, in conjunction with posterior surface molds, to form the lens of the invention using a suitable liquid lens-forming material placed between the molds followed by compression and curing of the lens-forming material.

Preferably, an ophthalmic lens of the invention or the optical tool to be used for making the same is fabricated by using a numerically controlled lathe, for example, such as Optoform® ultra-precision lathes (models 30, 40, 50 and 80) having Variform® or Varimax piezo-ceramic fast tool servo attachment from Precitech, Inc, according to a method described in a co-pending U.S. patent application of CibaVision, entitled Method for Manufacturing a contact lens, (U.S. Ser. No. 60/398,495, filed on Jul. 24, 2002), herein incorporated by reference in its entirety.

As an illustrative example, production of a contact lens having a ramped ridge zone as shown in FIG. 1 can occur from the following steps. First, a user defines a set of parameters, such as a surface tolerance, a concentricity tolerance, orientation of the lens design, the number of spokes to be generated for each of the anterior and posterior surfaces, creating zero point at 0,0, orientation of Z-axis, and type of lens surface (concave or convex surface) to be converted into a geometry. A "surface tolerance" refers to the allowed position-deviation of a projected point from an ideal position on a surface of a lens design. The deviation can be in the direction either parallel or perpendicular to the central axis of a lens design. A "concentricity tolerance" refers to the allowed deviation of a point from a given arc. A "spoke" refers to a ray radiating outwardly from the central axis and is perpendicular to the central axis. A "semi-diameter spoke" refers to a line segment from the central axis to the edge of a lens design. "Evenly-spaced semi-diameter spokes" means that all semi-diameter spokes radiate outwardly from the central axis and separate from each other by one equal angle. A "point spacing" refers to a distance between two points along the semi-diameter spoke.

Second, a user determines the number of points to be projected onto the a surface of the lens design (for example, the anterior surface) along each of the number of evenly-spaced semi-diameter spokes in a direction parallel to the central axis. A semi-diameter spoke at an azimuthal angle, at which one of the two bumps of the anterior surface is located, is selected as the semi-diameter probing spoke. Evenly-spaced points are projected along the semi-diameter probing spoke, in which each pair of points are separated by a point spacing of 10 microns. Then all of the projected points are divided into a series of groups, with each group composed of three consecutive points, a first point, a middle point, and a third point. Each of the points can belong to either one group or two groups. One group is analyzed at a time from the central axis to the edge, or from the edge to the central axis, from the curvature of the surface at the middle point of the group by comparing a distance between the middle point and a line linking the first point and the third point of the corresponding group with the predetermined surface tolerance. If the distance between the middle point and the line linking the first and third points of the group is larger than the predetermined surface tolerance, the curvature of the surface at that point is sharp and an additional point is projected between the first and the middle points in that group. The point spacing between the first and additional points is equal to point spacing between the additional and middle points. After adding an additional point, all of the points included the newly added point is regrouped again and the curvature of the surface at the middle point of each of the series of groups is analyzed. Such iterative procedure is repeated until the distance between the middle point of each of the series of groups and the line linking the first and the third points of corresponding group along the probing spoke is equal to or less than the predetermined surface tolerance. In this manner, the number of the points to be projected onto the surface of the lens design along each of the desired number of evenly-spaced semi-diameter spokes and point spacing for a series of pairs of neighboring points are determined.

The above-determined number of points is then projected onto the anterior surface of the lens design along each of 24, 96 or 384 semi-diameter spokes. For each of the semi-diameter spokes, a semi-meridian that is continuous in first derivative is generated. The semi-meridian includes a series of arcs and, optionally, straight lines wherein each arc is defined by fitting at least three consecutive points into a spherical mathematical function within a desired concentricity tolerance. Each of the straight lines is obtained by connecting at least three consecutive points. Preferably, the arc-fitting routine is started from the central axis to the edge. Similarly, conversion of the posterior surface of the lens design into a geometry can be carried out according to the above described procedure.

After converting the lens design to a geometry of a contact lens to be produced in a manufacturing system, a mini-file containing both the information for the header and the information about the geometry of the lens is generated. This mini-file also contains a zero semi-meridian that is based on the average height of each of the other meridians at each of radial locations and that gives the Variform a zero position on which it can base its oscillation calculations. In this mini-file, all semi-meridians have the same number of zones. This is accomplished by copying the last zone of a semi-meridian for a number of time to equalize the numbers of zones for all meridians. After the mini-file is complete, it is loaded into an Optoform® ultra-precision lathe (models 30, 40, 50 or 80) having Variform® piezo-ceramic fast tool servo attachment and run to produce a contact lens of the invention.

The present invention, in a further aspect, provides a method for producing an ophthalmic lens of the invention. The method comprises the step of producing an ophthalmic lens by a manufacturing means, wherein the ophthalmic lens comprises an optical zone, the optical zone having a first surface and an opposite of second surface and including a coma-like wavefront aberration oriented vertically from the top to the bottom of the ophthalmic lens. The vertically oriented coma-like wavefront aberration is introduced for minimizing/correcting presbyopia or for alleviating stress incurred in the accommodation of eye interfering with the emmetropization process(e.g., for anti-myopic lens).

An ophthalmic lens of the invention can be characterized by any known suitable optical metrology system. The vertically oriented coma-like and other wavefront aberrations of the lens can be determined by any suitable methods known to one skilled in the art, including without limitation, Shack-Hartmann techniques, Tscherning techniques, retinal ray-tracing techniques, and spatially-resolved refractometer techniques.

The present invention, in a still further aspect, provides a method for correcting or minimizing presbyopia. The method of the invention comprises the step of reshaping the cornea of an eye to produce a vertically oriented coma-like wavefront aberration.

The shape of the cornea can be modified through various methods. One method according to the invention is to control energy distribution of a laser beam on an optical surface of the cornea. Another method, according to the invention, is to control a flying spot laser pattern on the optical surface of the cornea. Yet another method, according to the invention, is to control angle of ablation on the optical surface of the cornea. Yet another method, according to the invention, is to ablate the cornea according to a mathematical model.

The above described embodiments are given as illustrative examples only. It will be readily appreciated that many deviations may be made from the specific embodiments disclosed in this specification without departing from the invention. Accordingly, the scope of the invention is to be determined by the claims below rather than being limited to the specifically described embodiments above.

We claim:

1. An ophthalmic lens comprising an optical zone, wherein the optical zone has a first surface and an opposite second surface and includes a coma-like wavefront aberration oriented vertically from the top to the bottom of the lens, wherein the coma-like wavefront aberration is, or is an equivalent of, a wavefront aberration described by any one of third order, fifth order, seventh order Zernike coma-like terms, and combinations thereof in proposed OSA Standard (Optical Society of America) Zernike Polynomials.

2. The ophthalmic lens of claim 1, wherein at least one of the first and second surface of the optical zone is asymmetrical, and wherein the optical zone has an optical power increasing from the top to the bottom of the optical zone.

3. The ophthalmic lens of claim 2, wherein at least one of the first surface and second surface of the optical zone is described by a spline-based mathematical function or a combination of two or more mathematical functions.

4. The ophthalmic lens of claim 3, wherein at least one of the first surface and second surface of the optical zone is described by a combination of two or more mathematical functions including Zernike polynomials.

5. The ophthalmic lens of claim 3, wherein at least one of the first surface and second surface of the optical zone is described by a combination of a biconic mathematical function with at least one vertically oriented coma-like Zernike term or equivalents thereof.

6. The ophthalmic lens of claim 5, wherein the magnitude of the vertically oriented Zernike coma coefficient, based on the proposed OSA Zernike standard, is between about 0.1 µm RMS (root-mean-square) and about 2 µm RMS at a 6 mm diameter optical zone.

7. The ophthalmic lens of claim 5, wherein said at least one vertically oriented coma-like Zernike term is a vertically oriented third order coma-like Zernike term Z7 (based on the proposed OSA Standard Zernike Polynomials), and wherein said at least one of the first surface and second surface of the optical zone is described by the following equation:

$$Z(\rho, \theta) := \frac{(c_x \bullet r^2 + c_y \bullet r^2)}{[1 + \sqrt{1 - (1+k_x) \bullet (c_x^2 \bullet r^2) - (1+k_y) \bullet c_y^2 \bullet r^2\}}]} +$$
$$Z7 \bullet \sqrt{8} \bullet (3 \bullet \rho^2 - 2) \bullet \rho \bullet \sin(\theta)$$

wherein, $Z(\rho, \theta)$ describes the optical zone, $c_x$ is the curvature (reciprocal of the radius) in x' direction, $c_y$ is the curvature (reciprocal of the radius) in y' direction, $k_x$ x is a conic constant in x' direction, $k_y$ is a conic constant in y' direction, r equals to the semi diameter of the at least one surface, $\rho$ is equivalent to the normalized pupil coordinate (r/rmax), $\theta$ is angular component, Z7 is coefficient of vertical coma in terms of RMS μm.

8. The ophthalmic lens of claim 5, wherein said at least one vertically oriented coma-like Zernike term is a vertically oriented fifth order coma-like Zernike term Z17.

9. The ophthalmic lens of claim 5, wherein said at least one vertically oriented coma-like Zernike term is a vertically oriented seventh order coma-like term Z31.

10. The ophthalmic lens of claim 3, wherein at least one of the first surface and second surface of the optical zone is described by a combination of a conic mathematical function with at least one vertically oriented coma-like Zernike term or equivalents thereof.

11. The ophthalmic lens of claim 10, wherein said at least one vertically oriented coma-like Zernike term is a vertically oriented third order coma-like Zernike term Z7, Z17 or seventh order coma-like term Z31 (based on the proposed OSA Standard Zernike Polynomials).

12. The ophthalmic lens of claim 3, wherein at least one of the first surface and second surface of the optical zone is described by one or more spline-based mathematical functions.

13. The ophthalmic lens of claim 3, wherein the ophthalmic lens is a contact lens.

14. The ophthalmic lens of claim 13, wherein the contact lens comprises one or more orientation or stabilization features.

15. The ophthalmic lens of claim 14, wherein said one or more orientation/stabilization features are selected from the group consisting of: a prism ballast or the like that uses a varying thickness profile to control the lens orientation; a faceted surface in which parts of the lens geometry is removed to control the lens orientation; a ridge feature which orients the lens by interacting with the eyelid; double slab-off features which have a top slab-off zone and a bottom slab-off zone zones to maintain the lens orientation on the eye; and non-prism ballast features in the peripheral zone of the lens, the peripheral zone surrounding the optical zone of the lens.

16. The ophthalmic lens of claim 14, wherein the contact lens comprises on the anterior surface of the lens a ramped ridge zone which is disposed below the optical zone and includes an upper edge, a lower ramped edge, a latitudinal ridge that extends outwardly from the anterior surface, and a ramp that extends dowardly from the lower ramped edge and has a curvature or slope that provides a varying degree of interaction between the ramped ridge zone and the lower eyelid of an eye depending on where the lower eyelid strikes the ramped ridge zone.

17. The ophthalmic lens of claim 14, wherein the contact lens comprises:

a posterior surface; and an opposite anterior surface including a vertical meridian, a horizontal meridian, an anterior optical zone, a blending zone extending outwardly from the anterior optical zone, a peripheral zone surrounding the blending zone, and an edge zone circumscribing and tangent to the peripheral zone, wherein the anterior optical zone is one of the first and second surface of the optical zone, wherein the blending zone has a surface which ensures that the peripheral zone, the blending zone and the anterior optical zone are tangent to each other, wherein the peripheral zone has a surface that, in combination with the posterior surface, provides in the peripheral zone of the lens a thickness profile which is characterized (1) by having a lens thickness which increases progressively from the top of the lens downwardly along each of the vertical meridian and lines parallel to the vertical meridian until reaching a maximum value at a position between the anterior optical zone and the edge zone and then decreases to the edge of the edge zone, or (2) by having a mirror symmetry with respect to a plane cutting through the vertical meridian, by having a substantially constant thickness in a region around the horizontal meridian and by having a thickness which decreases progressively from the horizontal meridian to the top or bottom of the contact lens along each of the vertical meridian and lines parallel to the vertical meridian.

18. The ophthalmic lens of claim 3, wherein the ophthalmic lens is a phakic or aphakic intraocular lens.

19. The ophthalmic lens of claim 18, wherein the phakic or aphakic intraocular lens comprises haptics.

20. A customized ophthalmic lens, comprising an optical zone which, alone or in combination with the optics of an eye, produce a vertically oriented coma-like wavefront aberration, wherein the coma-like wavefront aberration is, or is an equivalent of, a wavefront aberration described by any one of third order, fifth order, seventh order Zernike coma-like terms, and combinations thereof in proposed OSA Standard (Optical Society of America) Zernike Polynomials.

21. The customized ophthalmic lens of claim 20, wherein the optical zone does not correct the vertically oriented coma-like aberrations of the eye while correcting or minimizing wavefront aberration other than the vertically oriented coma-like aberrations.

22. The customized ophthalmic lens of claim 21, wherein the optical zone has a vertically oriented coma-like wavefront aberration introduced to reach a desired overall amount of vertically oriented coma-like wavefront aberrations of the ophthalmic lens plus the eye.

23. The customized ophthalmic lens of claim 20, correct all or parts of each of dominant high order wavefront aberrations of the eye so as to obtain a vertically oriented coma-like wavefront aberration.

24. The customized ophthalmic lens of claim 23, wherein the optical zone has a vertically oriented coma-like wavefront aberration introduced to reach a desired overall amount of vertically oriented coma-like wavefront aberrations of the ophthalmic lens plus the eye.

25. The customized ophthalmic lens of claim 20, wherein the ophthalmic lens is a contact lens.

26. The customized ophthalmic lens of claim 25, wherein the posterior surface of the contact lens has a geometry to accommodate the corneal topography of the eye or a corneal topography statistically represent a segment of population.

27. The customized ophthalmic lens of claim 25, wherein the contact lens comprises one or more orientation/stabilization features.

28. The customized ophthalmic lens of claim 27, wherein said one or more orientation/stabilization features are selected from the group consisting of: a prism ballast or the like that uses a varying thickness profile to control the lens orientation; a faceted surface in which parts of the lens geometry is removed to control the lens orientation; a ridge feature which orients the lens by interacting with the eyelid; double slab-off features which have a top slab-off zone and a bottom slab-off zone zones to maintain the lens orientation on the eye; and non-prism ballast features in the peripheral zone of the lens, the peripheral zone surrounding the optical zone of the lens.

29. The customized ophthalmic lens of claim 28, wherein the contact lens comprises on the anterior surface of the lens a ramped ridge zone which is disposed below the optical zone and includes an upper edge, a lower ramped edge, a latitudinal ridge that extends outwardly from the anterior surface, and a ramp that extends dowardly from the lower ramped edge and has a curvature or slope that provides a varying degree of interaction between the ramped ridge zone and the lower eyelid of an eye depending on where the lower eyelid strikes the ramped ridge zone.

30. The customized ophthalmic lens of claim 28, wherein the anterior surface of the contact lens includes a vertical meridian, a horizontal meridian, an anterior optical zone, a blending zone extending outwardly from the anterior optical zone, a peripheral zone surrounding the blending zone, and an edge zone circumscribing and tangent to the peripheral zone, wherein the anterior optical zone is one of the first and second surface of the optical zone, wherein the blending zone has a surface which ensures that the peripheral zone, the blending zone and the anterior optical zone are tangent to each other, wherein the peripheral zone has a surface that, in combination with the posterior surface, provides in the peripheral zone of the lens a thickness profile which is characterized (1) by having a lens thickness which increases progressively from the top of the lens downwardly along each of the vertical meridian and lines parallel to the vertical meridian until reaching a maximum value at a position between the anterior optical zone and the edge zone and then decreases to the edge of the edge zone, or (2) by having a mirror symmetry with respect to a plane cutting through the vertical meridian, by having a substantially constant thickness in a region around the horizontal meridian and by having a thickness which decreases progressively from the horizontal meridian to the top or bottom of the contact lens along each of the vertical meridian and lines parallel to the vertical meridian.

31. The customized ophthalmic lens of claim 20, wherein the ophthalmic lens is a phakic intraocular lens or an aphakic intraocular lens.

32. A method for making an ophthalmic lens, comprising the step of producing the ophthalmic lens by a manufacturing means, wherein the ophthalmic lens comprises an optical zone, the optical zone having a first surface and an opposite second surface and including a coma-like wavefront aberration oriented vertically from the top to the bottom of the lens, wherein the coma-like wavefront aberration is, or is an equivalent of, a wavefront aberration described by any one of third order, fifth order, seventh order Zernike coma-like terms, and combinations thereof in proposed OSA Standard (Optical Society of America) Zernike Polynomials.

33. The method of claim 32, wherein at least one of the first and second surface of the optical zone is asymmetrical, and wherein the optical zone has an optical power increasing from the top to the bottom of the optical zone.

34. The method of claim 33, wherein at least one of the first and second surface of the optical zone is asymmetrical, and wherein the optical zone has an optical power increasing from the top to the bottom of the optical zone.

35. The method of claim 34, wherein at least one of the first surface and second surface of the optical zone is described by a spline-based mathematical function or a combination of two or more mathematical functions.

36. The method of claim 35, wherein at least one of the first surface and second surface of the optical zone is described by a combination of two or more mathematical functions including Zernike polynomials.

37. The method of claim 36, wherein said at least one of third, fifth and seventh order coma-like Zernike term is a vertically oriented third order coma-like Zernike term Z7, fifth order coma-like Zernike term Z17 or seventh order coma-like term Z31 based on the proposed OSA Standard Zernike Polynomials.

38. The method of claim 35, wherein at least one of the first surface and second surface of the optical zone is described by one or more spline-based mathematical functions.

39. The method of claim 35, wherein the manufacturing means is a computer-controllable manufacturing device.

40. The method of claim 39, wherein the computer controllable manufacturing device is a numerically controlled lathe.

41. A method for minimizing or correcting presbyopia, comprising the step of reshaping a cornea of an eye to produce a vertically oriented coma-like wavefront aberration.

42. The method of claim 41, wherein the reshaped cornea has an optical zone, wherein the optical zone is asymmetrical, and has an optical power increasing from the top to the bottom of the optical zone.

43. The method of claim 42, wherein the optical zone is described by a spline-based mathematical function or a combination of two or more mathematical functions.

44. The method of claim 43, wherein the optical zone is described by a combination of two or more mathematical functions including Zernike polynomials.

45. The method of claim 44, wherein the Zernike polynomials include at least one of third, fifth and seventh order coma-like terms based on the proposed OSA Zernike standard.

46. The method of claim 45, wherein said at least one of third, fifth and seventh order coma-like Zernike term is a vertically oriented third order coma-like Zernike term Z7, fifth order coma-like Zernike term Z17 or seventh order coma-like term Z31 based on the proposed OSA Standard Zernike Polynomials.

47. The method of claim 46, wherein the optical zone is described by a combination of a biconic mathematical function with at least one of the vertically oriented coma-like Zernike terms or equivalents thereof.

48. The method of claim 47, wherein the magnitude of the vertically oriented Zernike coma coefficient, based on the proposed OSA Zernike standard, is between about 0.1 µm RMS (root-mean-square) and about 2 µm RMS at a 6 mm diameter optical zone.

49. The method of claim 47, wherein said at least one of the vertically oriented coma-like Zernike terms is a vertically oriented third order coma-like Zernike term Z7 based on the proposed OSA Standard Zernike Polynomials, and wherein the optical zone is described by the following equation:

$$Z(\rho, \theta) := \frac{(c_x \bullet r^2 + c_y \bullet r^2)}{[1 + \sqrt{1 - (1+k_x)\bullet(c_x^2 \bullet r^2) - (1+k_y)\bullet c_y^2 \bullet r^2\}}]} +$$
$$Z7 \bullet \sqrt{8} \bullet (3 \bullet \rho^2 - 2) \bullet \rho \bullet \sin(\theta)$$

wherein, $Z(\rho, \theta)$ describes the optical zone,
$c_x$ is the curvature (reciprocal of the radius) in x' direction,
$c_y$ is the curvature (reciprocal of the radius) in y' direction,
$k_x$ is a conic constant in x' direction,
$k_y$ is a conic constant in y' direction,
r equals to the semi diameter of the at least one surface,
$\rho$ is equivalent to the normalized pupil coordinate (r/rmax),
$\theta$ is angular component,
Z7 is coefficient of vertical coma in terms of RMS μm.

50. The method of claim 46, wherein the optical zone is described by a combination of a conic mathematical function with at least one vertically oriented coma-like Zernike term or equivalents thereof.

51. The method of claim 50, wherein said at least one vertically oriented coma-like Zernike term is a vertically oriented third order coma-like Zernike term Z7, Z17 or seventh order coma-like term Z31 based on the proposed OSA Standard Zernike Polynomials.

52. The method of claim 46, wherein the optical zone is described by one or more spline-based mathematical functions.

53. The method of claim 43, wherein the step of reshaping occurs by ablating the cornea.

54. The method of claim 53, wherein the step of ablating occurs by controlling energy distribution of a laser beam on an optical surface of the cornea.

55. The method of claim 53, wherein the step of ablating occurs by controlling a flying spot laser pattern on an optical surface of the cornea.

56. The method of claim 53, wherein the step of ablating occurs by controlling angle of ablation on an optical surface of the cornea.

* * * * *